(12) United States Patent
Polymeropoulos et al.

(10) Patent No.: US 9,987,264 B2
(45) Date of Patent: *Jun. 5, 2018

(54) METHOD AND COMPOSITION FOR TREATING A SEROTONIN RECEPTOR-MEDIATED CONDITION

(71) Applicant: Vanda Pharmaceuticals Inc., Washington, DC (US)

(72) Inventors: Mihael H. Polymeropoulos, Potomac, MD (US); Paolo Baroldi, Potomac, MD (US); Curt Wolfgang, Germantown, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/242,468

(22) Filed: Aug. 19, 2016

(65) Prior Publication Data

US 2016/0361303 A1    Dec. 15, 2016

Related U.S. Application Data

(63) Continuation of application No. 14/088,877, filed on Nov. 25, 2013, now Pat. No. 9,446,038, which is a continuation of application No. 12/747,912, filed on Oct. 28, 2010, now Pat. No. 8,618,134.

(60) Provisional application No. 61/013,377, filed on Dec. 13, 2007.

(51) Int. Cl.
*A61K 31/454* (2006.01)
*A61K 31/445* (2006.01)
*A61K 45/06* (2006.01)

(52) U.S. Cl.
CPC .......... *A61K 31/454* (2013.01); *A61K 31/445* (2013.01); *A61K 45/06* (2013.01)

(58) Field of Classification Search
CPC .................................................. A61K 31/454
See application file for complete search history.

(56) References Cited

U.S. PATENT DOCUMENTS

| | | | |
|---|---|---|---|
| 4,772,475 A | 9/1988 | Fukui et al. | |
| 5,364,866 A | 11/1994 | Strupczewski et al. | |
| 5,658,911 A | 8/1997 | Strupczewski et al. | |
| 5,968,544 A | 10/1999 | Beiman et al. | |
| 6,140,345 A | 10/2000 | Strupczewski et al. | |
| 6,312,728 B1 | 11/2001 | Beiman et al. | |
| 6,500,454 B1 | 12/2002 | Percel et al. | |
| 6,627,223 B2 | 9/2003 | Percel et al. | |
| 6,663,888 B2 | 12/2003 | Percel et al. | |
| 8,618,134 B2 | 12/2013 | Polymeropoulos et al. | |
| 8,729,100 B2 | 5/2014 | Polymeropoulos et al. | |
| 9,446,038 B2 * | 9/2016 | Polymeropoulos | A61K 31/445 |
| 2003/0091645 A1 | 5/2003 | Ahlheim et al. | |
| 2009/0298880 A1 | 12/2009 | Wolfgang et al. | |

FOREIGN PATENT DOCUMENTS

| | | |
|---|---|---|
| CA | 2605224 A1 | 10/2006 |
| WO | 03054226 A2 | 7/2003 |
| WO | 2004006886 A2 | 1/2004 |
| WO | 2005012254 A1 | 2/2005 |
| WO | 2006039663 A2 | 4/2006 |
| WO | 2006055734 A2 | 4/2006 |
| WO | 2006108519 A1 | 10/2006 |
| WO | 03020707 A1 | 3/2013 |

OTHER PUBLICATIONS

PCT International Search Report and Written Opinion for corresponding PCT Application No. PCT/US2008/086733 dated Jun. 24, 2010, 6 pages.
PCT International Search Report and Written Opinion for corresponding PCT Application No. PCT/US2008/086733 dated Feb. 9, 2009, 13 pages.
Hosoda et al., "Blockade of both a1A and a1B-adrenergic receptor subtype signaling is required to inhibit neointimal formation in the mouse femoral artery," Mar. 2007, pp. H514-H519, Am J Physiol Heart Circ Physiol 293.
Subramanian et al., "Receptor profile of P88-8991 and P95-12113, metabolites of the novel antipsychotic iloperidone," Jan. 2002, Progress in Neuro-Psychopharmacology & Biological Psychiatry, pp. 553-560, XP008087896.
Office Action for European Application No. 08 859 451.0-2123 dated Sep. 27, 2011, 4 pages.
International Search Report and Written Opinion for corresponding Singapore Patent Application No. 201004139-0, dated Sep. 22, 2011, 18 pages.
Mehta et al., "Coated Pellets Under the Microscope," Pharmaceutical Technology, Jun. 1985, 7 pages.
Lalla et al., "Controlled-Release Isosorbide Dinitrate Pellets. Part I: Design and Evaluation of Controlled-Release Capsule Dosage Form," Journal of Pharmaceutical Sciences, vol. 82, No. 12, Dec. 1993, 3 pages.
Lalla et al., "Controlled-Release Isosorbide Dinitrate Pellets. Part II: In Vivo Studies," Journal of Pharmaceutical Sciences, vol. 82, No. 12, Dec. 1993, 3 pages.
U.S. Appl. No. 12/747,911 Final Office Action dated Aug. 12, 2013, 14 pages.
U.S. Appl. No. 12/747,911, Notice of Allowance dated Jan. 7, 2014, 6 pages.
U.S. Appl. No. 12/747,911, Office Action dated Feb. 1, 2013, 26 pages.
Kalkman et al., "Extended radioligand binding profile of iloperidone: a broad spectrum dopamine/serotonin/norepinephrine receptor antagonist for the management of psychotic disorders," Neuropsychopharmacology. 25 (6):904-14 (2001).
Rosel et al., "Different distributions of the 5-HT reuptake complex and the postsynaptic 5-HT2A receptors in Brodmann areas and brain hemispheres," 2002, pp. 105-115, Psychiatry Research, vol. 111.

(Continued)

*Primary Examiner* — James D. Anderson
(74) *Attorney, Agent, or Firm* — Hoffman Warnick LLC

(57) ABSTRACT

A method and composition for treating serotonin receptor-mediated conditions.

14 Claims, No Drawings

(56) References Cited

OTHER PUBLICATIONS

Markel et al., "Increased platelet adhesion and aggregation in hypertensive patients: effect of atenolol" Br. J. Clin. Pharmac. (1983), 16, pp. 663-668.
U.S. Appl. No. 14/088,877, Office Action dated Aug. 6, 2015, 18 pages.
International Search Report and the Written Opinion for corresponding PCT Application No. PCT/US2008/086734, dated Mar. 3, 2009, 14 pages.
International Search Report and Written Opinion for corresponding Singapore Application No. 201004140-8, dated Sep. 9, 2011, 19 pages.
International Search Report and Written Opinion for corresponding PCT Application No. PCT/US2008/086734, dated Jun. 24, 2010, 8 pages.
U.S. Appl. No. 12/747,912, Final Office Action dated Apr. 19, 2013, 17 pages.
U.S. Appl. No. 12/747,912, Office Action dated Nov. 6, 2012, 18 pages.
U.S. Appl. No. 12/747,912, Notice of Allowance dated Aug. 21, 2013, 10 pages.
Nash "Alpha-adrenergic blockers: mechanism of action, blood pressure control, and effects of lipoprotein metabolism," Clin Cardiol. 13(11):764-72 (1990).
PROPECIA® Prescribing Information 2004 (available from FDA website as the 2004 Prescribing Information www.accessdata.fda.gov/drugsatfda_docs/label/2004/20788s002,010,011lbl.pdf).
Quan et al., "Androgens augment proximal tubule transport," Am J Physiol Renal Physiol. 287(3):F452-9 (2004).
Sainati et al., "Safety, tolerability, and effect of food on the pharmacokinetics of iloperidone (HP 873), a potential atypical antipsychotic," J Clin Pharmacol. 35(7):713-20 (1995). Abstract only.
U.S. Appl. No. 14/088,877, Final Office Action 1 dated Feb. 3, 2016, 21 pages.
U.S. Appl. No. 14/088,877, Notice of Allowance dated May 26, 2016, 7 pages.
Office Action and English Translation thereof for Australian Patent Application No. 2015275276 dated Sep. 19, 2016, 4 pages.
Liolitsa et al. "Association study of the 5-HT2A receptor gene polymorphism, T102C and essential hypertension," Journal of Human Hypertension, 2001, 15, 335-339.

\* cited by examiner

METHOD AND COMPOSITION FOR TREATING A SEROTONIN RECEPTOR-MEDIATED CONDITION

CROSS-REFERENCE TO RELATED APPLICATIONS

This application is a continuation of co-pending U.S. patent application Ser. No. 14/088,877, filed 25 Nov. 2013, which is a continuation of U.S. patent application Ser. No. 12/747,912, filed 12 Jun. 2010, now U.S. Pat. No. 8,618,134, which is the US National Phase of PCT/2008/086734, filed 13 Dec. 2008, which claims priority to U.S. Provisional Patent Application Ser. No. 61/013,377, filed 13 Dec. 2007, each of which is hereby incorporated herein as though fully set forth.

BACKGROUND OF THE INVENTION

Technical Field

This invention relates generally to the treatment of serotonin (5-hydroxytryptamide, 5-HT) receptor-mediated conditions, and more specifically, to pharmaceutical compositions and methods for treating such conditions. Such methods include administering to an animal a therapeutically effective dose of 4-[3-[4-(6-fluoro-1,2,-benzisoxazol-3-yl)-1-piperidinyl]propoxy]-3-methoxy-benzoic acid, a metabolite of iloperidone.

SUMMARY OF THE INVENTION

The invention provides a method and composition for treating serotonin receptor-mediated conditions, including, but not limited to, platelet aggregation, coronary artery disease, myocardial infarction, transient ischemic attacks, stable angina, unstable angina, thrombotic stroke, a secondary ischemic event (e.g., reversible ischemic neurological deficit and intermittent claudication), atrial fibrillation, thrombosis (e.g., clot formation associated with angioplasty, cardiac surgery, and/or atrial fibrillation), restenosis (including, e.g., by treatment with a medicated device, such as a medicated stent), asthma, and pathologies associated with diabetes (e.g., diabetic nephropathy and diabetic retinopathy).

A first aspect of the invention provides a method for antagonizing a serotonin (5-hydroxytryptamine 2A, 5-HT$_{2A}$) receptor in an animal suffering a condition that is mediated by a 5-HT$_{2A}$ receptor, the method comprising: internally administering to the animal an effective amount of 4-[3-[4-(6-fluoro-1,2,-benzisoxazol-3-yl)-1-piperidinyl]propoxyl-]-3-methoxy-benzoic acid, or pharmaceutically-acceptable salt thereof.

A second aspect of the invention provides a method for treating in an animal a condition associated with platelet aggregation, the method comprising: internally administering to the animal an effective amount of 4-[3-[4-(6-fluoro-1,2,-benzisoxazol-3-yl)-1-piperidinyl]propoxyl]-3-methoxy-benzoic acid or pharmaceutically-acceptable salt thereof.

A third aspect of the invention provides a method for treating in an animal a recurrent ischemic event, the method comprising: internally administering to the animal an effective amount of 4-[3-[4-(6-fluoro-1,2,-benzisoxazo1-3-yl)-1-piperidinyl]propoxyl]-3-methoxy-benzoic acid or pharmaceutically-acceptable salt thereof.

A fourth aspect of the invention provides the use of 4-[3-[4-(6-fluoro-1,2,-benzisoxazol-3-yl)-1-piperidinyl] propoxyl]-3-methoxy-benzoic acid or a pharmaceutically-acceptable salt thereof for use in, or for the manufacture of a medicament useful in, treating a condition mediated by a serotonin (5-hydroxytryptamine, 5-HT) receptor.

DETAILED DESCRIPTION

As indicated above, the invention provides compositions and methods for treating serotonin receptor-mediated conditions. Methods according to the invention include administering to an animal an effective amount of 4-[3-[4-(6-fluoro-1,2,-benzisoxazol-3-yl)-1-piperidinyl]propoxyl]-3-methoxy-benzoic acid, or a pharmaceutically acceptable salt thereof, alone or in combination with one or more additional active agents, such as an antithrombotic agent.

As used herein, "effective amount" shall mean an amount that prevents or delays onset of signs and symptoms of the condition being treated for, or that eliminates or alleviates, i.e., lessens the severity or reduces the frequency of occurrence, of signs and symptoms of the condition. In addition, "treatment," "treating," and "treat" shall mean treatment or prevention, i.e., the treatment or prevention of an serotonin receptor-mediated condition.

As used herein, "agonist" shall mean a moiety that activates the intracellular response when it binds to a receptor, or enhances GTP binding to membranes.

As used herein, "partial agonist" shall mean a moiety which activates the intracellular response when it binds to a receptor to a lesser degree/extent than does an agonist, or enhances GTP binding to membranes to a lesser degree/extent than does an agonist.

As used herein, "antagonist" shall mean a moiety that competitively binds to a receptor at the same site as an agonist but which does not activate the intracellular response initiated by the active form of the receptor, and can thereby inhibit the intracellular responses by agonists or partial agonists. Antagonists do not diminish the baseline intracellular response in the absence of an agonist or partial agonist.

As used herein, "inverse agonist" shall mean a moiety that binds to the endogenous form of a receptor or the constitutively activated form of the receptor, and which inhibits the baseline intracellular response initiated by the active form of the receptor below the normal base level of activity which is observed in the absence of agonists or partial agonists, or decreases GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The present invention contemplates use of a compound of 4-[3-[4-(6-fluoro-1,2,-benzisoxazol-3-yl)-1-piperidinyl] propoxyl]-3-methoxy-benzoic acid or a pharmaceutically acceptable salt thereof, as well as esters, stereoisomers, solvates, hydrates, crystalline and amorphous forms, and polymorphs thereof.

4-[3-[4-(6-fluoro-1,2,-benzi soxazol-3-yl)-1-piperidinyl] propoxy]-3-methoxy-benzoic acid is a metabolite of iloperidone. Iloperidone is disclosed in U.S. Pat. Nos. 5,364,866, 5,658,911, and 6,140,345, each of which is incorporated herein by reference. In some cases, it may be advantageous to use iloperidone or an iloperidone metabolite preferentially in patients with certain genotypes, as disclosed, e.g., in International Patent Application Publication Nos. WO2006039663 and WO2003054226, which are also incorporated herein by reference.

4-[3-[4-(6-fluoro-1,2,-benzisoxazol-3-yl)-1-piperidinyl] propoxy]-3-methoxy-benzoic acid is highly selective for and potent with respect to alpha 1 adrenoceptors and $5HT_{2A}$; on the whole, it has slightly greater affinity/potency for alpha 1 adrenoceptors than for alpha 2 adrenoreceptors and has very weak if any activity with respect to the dopamine, histamine, and serotonin receptors (other than $5HT_{2A}$).

In a radioligand binding study, 4-[3-[4-(6-fluoro-1,2,-benzisoxazol-3-yl)-1-piperidinyl]propoxy]-3-methoxy-benzoic acid had the following activity against the human $5HT_{2A}$ receptor:

| Conc (uM) | % Inhibition | $IC_{50}$ (uM) | Ki (nM) | $n_H$ |
|---|---|---|---|---|
| .03 | 66 | .0137 +/− .001 | 3.91 +/− .267 | 1.05 +/− .091 |

The $IC_{50}$ against other serotonin receptors ranged from about 1.5 to about 10.4 uM. The $IC_{50}$ against dopamine and histamine H1 receptors ranged from about 1.3 to about 8.0 uM. The $IC_{50}$ against alpha 1 and 2 adrenergic receptors ranged from about 0.01 to about 4.9 uM. After the alpha 1B adrenoceptor (rat), greatest potency was observed against the human serotonin $5HT_{2A}$ receptor.

Furthermore, 4-[3-[4-(6-fluoro- 1,2,-benzisoxazol-3 -yl)-1-piperidinyl]propoxyl]-3 -methoxy-benzoic acid has demonstrated a dose-dependent antagonist activity in a platelet aggregation assay. In this assay, platelet rich plasma was obtained from albino rabbits. Platelet aggregation was induced in the presence of 3 μM adenosine diphosphate (ADP) and was potentiated by the addition of 10 μM serotonin. 4-[3-[4-(6-fluoro-1,2,-benzisoxazol-3-yl)-1-piperidinyl]propoxyl]-3-methoxy-benzoic acid inhibited the platelet aggregation in the presence of serotonin within 5 minutes, by 30, 50, 60, and 79% at the concentrations of 6 μM, 60 μM, 0.6 mM, and 1 mM, respectively. Ketanserin (100 μM), a well known $5-HT_{2A}$ receptor antagonist used as a positive control in this assay, demonstrated a 55% inhibitory effect in the same conditions.

4-[3-[4-(6-fluoro-1,2,-benzisoxazol-3 -yl)-1-piperidinyl] propoxyl]-3-methoxy-benzoic acid appears not to cross the blood-brain barrier. Specifically, in DMPK studies using rats treated with [14C] 4-[3-[4-(6-fluoro-1,2,-benzisoxazol-3-yl)-1-piperidinyl]propoxyl]-3-methoxy-benzoic acid, none of the animals had measurable radioactivity concentrations in the brain. Therefore, 4-[3-[4-(6-fluoro-1,2,-benzisoxazol-3-yl)-1-piperidinyl]propoxyl]-3-methoxy-benzoic acid is particularly useful in conditions that are not mediated, to a substantial degree, by receptors in the brain.

A method according to the invention includes administering to an animal suffering from a $5-HT_{2A}$ receptor-mediated condition an effective amount of 4-[3-[4-(6-fluoro-1, 2,-benzisoxazol-3-yl)-1-piperidinyl]propoxyl]-3-methoxy-benzoic acid. In various embodiments, the condition may be, but is not limited to, platelet aggregation, coronary artery disease, myocardial infarction, transient ischemic attacks, stable angina, unstable angina, thrombotic stroke, a secondary ischemic event, atrial fibrillation, thrombosis, restenosis, asthma, and a pathology associated with diabetes.

4-[3-[4-(6-fluoro-1,2,-benzisoxazol-3-yl)- 1-piperidinyl] propoxyl]-3-methoxy-benzoic acid may be administered separately or together with an antithrombotic agent. Suitable antithrombic agents include, for example, clopidogrel bisulfate, streptokinase, alteplase, aprotinin, aspirin, and warfarin. An embodiment including an antithrombic agent may, for example, comprise a pill or capsule having both active pharmaceutical ingredients either admixed together or having each active pharmaceutical ingredient in a discrete portion of the pill or capsule. Metabolites, prodrugs, stereoisomers, polymorphs, hydrates, solvates, and salts of the above compounds that are directly or indirectly active can, of course, also be used in the practice of this invention.

Compounds administered according to the invention may take any number of forms, including, for example, tablets, capsules, oral solutions, intravenous solutions, intramuscular injectables, intradermal injectables, suppositories, patches, inhalents, and nasal sprays. Similarly, such compounds may be provided in immediate release formulations, extended release formulations, or long-term injectable formulations (e.g., 28 day depot formulations). In addition, methods according to the invention may include once-, twice-, or thrice-daily administrations.

An effective amount of 4-[3-[4-(6-fluoro-1,2,-benzisoxazol-3-yl)-1-piperidinyl]propoxyl]-3-methoxy-benzoic acid may be administered to a subject animal (typically a human but other animals, e.g., farm animals, pets and racing animals, can also be treated) by a number of routes. An effective amount is an amount that prevents or delays onset of signs and symptoms of the condition being treated for, or that eliminates or alleviates, i.e., lessens the severity or reduces the frequency of occurrence, of signs and symptoms of the $5HT_{2A}$ receptor-mediated condition.

An effective amount may vary quantitatively depending upon, e.g., the patient, the severity of the disorder or symptom being treated, and the route of administration. Such dose can be determined by routine studies. In general, for systemic administration, e.g., oral administration, an effective dose is expected to be in the range of about 1 to about 500 mg/day, e.g., 5-100 mg/day, or about 0.01 to about 10 mg/kg/day, e.g., 0.5-1.5 mg/kg/day.

It will be understood that the dosing protocol, including the amount of 4-[3-[4-(6-fluoro-1,2,-benzisoxazol-3-yl)-1-piperidinyl]propoxyl]-3-methoxy-benzoic acid actually administered, will be determined by a physician in the light of the relevant circumstances. These include, for example, the condition to be treated, the chosen route of administration, the age, weight, and response of the individual patient, and the severity of the patient's symptoms. Patients should of course be monitored for possible adverse events. For therapeutic or prophylactic use, 4-[3-[4-(6-fluoro-1,2,-benzisoxazol-3-yl)-1-piperidinyl]propoxyl]-3-methoxy-benzoic acid will normally be administered as a pharmaceutical composition comprising 4-[3-[4-(6-fluoro-1,2,-benzisoxazol-3-yl)-1-piperidinyl]propoxyl]-3-methoxy-benzoic acid as the (or an) essential active ingredient in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of iloperidone or an active metabolite thereof. See, for example, REMINGTON'S PHARMACEUTICAL SCIENCES, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier, which may be in the form of a capsule, sachet, paper, or other container. When the carrier serves as a diluent, it may be a solid, semi-solid, or liquid material which acts as a vehicle, excipient, or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

Some examples of suitable excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate, and mineral oil. The formulations can additionally include lubricating agents, wetting agents, emulsifying and suspending agents, preserving agents, sweetening agents, and/or flavoring agents. The compositions of the invention may be formulated so as to provide quick, sustained, or delayed release of the active ingredient after administration to the patient.

Administration of 4-[3-[4-(6-fluoro-1,2,-benzisoxazol-3-yl)-1-piperidinyl]propoxyl]-3-methoxy-benzoic acid or a pharmaceutically-acceptable salt thereof, according to any of the above embodiments, for treating BPH or for other indications, may be accomplished through the use of a controlled release pharmaceutical dosage form, e.g., delayed, sustained, or pulsatile release. By "controlled release" is meant that the absorption of the active pharmaceutical ingredient (API) is delayed, sustained or delayed and sustained relative to an immediate release oral form for administration by swallowing. Such a dosage form is disclosed, e.g., in U.S. Pat. No. 4,772,475,which is incorporated herein by reference.

For example, a controlled release formulation of the invention includes one in which: 4-[3-[4-(6-fluoro- 1,2,-benzisoxazol-3 -yl)-1-piperidinyl]propoxy]-3 -methoxy-benzoic acid or a pharmaceutically-acceptable salt thereof, dissolves at a rate of between about 3% and about 15% per hour, more preferably between about 4% and about 13% per hour, and most preferably between about 5% and about 7% per hour in a standard dissolution assay (e.g., an aqueous solvent at (1) pH 4.5, (2) pH 6.8 or (3) 0.1N HCl, at 37° C.), thereby providing a slow, substantially constant dosage of 4-[3-[4-(6-fluoro-1,2,-benzisoxazol-3-yl)-1-piperidinyl] propoxyl]-3-methoxy-benzoic acid or a pharmaceutically acceptable salt thereof over a period of between about 16 and about 24 hours. In another embodiment, 4-[3-[4-(6-fluoro-1,2,-benzisoxazol-3-yl)-1-piperidinyl]propoxy]-3-methoxy-benzoic acid or a pharmaceutically acceptable salt thereof is released in a pulsatile profile, e.g., to release approximately 25% of drug shortly following administration and approximately 25% of drug at more or less 2 hours, 4 hours, and 6 hours post-administration, or to release approximately 50% of drug shortly following administration and approximately 25% of drug at more or less 2 hours and 4 hours post-administration or to release approximately 50% of drug shortly following administration and approximately 25% of drug at more or less 4 hours and 6 hours post-administration.

The controlled release dosage forms of the present invention may employ a number of controlled release technologies for oral delivery. For example, Lalla and Bhat describe a method of coating DCP granules with the vasodilator isosorbide dinitrate to slow its release. Such method for preparing a pharmaceutical composition of the present invention in controlled release form comprises first spraying DCP granules with a sugar syrup and sorting the coated granules to select those having diameters between about 500 and about 600 μm. Next, a coating of 4-[3-[4-(6-fluoro-1, 2,-benzisoxazol-3-yl)-1-piperidinyl]propoxyl]-3-methoxy-benzoic acid or a pharmaceutically-acceptable salt or ester thereof ("active pharmaceutical ingredient" or "API") is sprayed onto the surfaces of the granules and the granules allowed to dry. A layer of an acidic buffering agent can be applied under and/or above the drug layer in order to maintain an acidic microenvironment in within the pellet matrix. Finally, a polymeric coating is applied to the dried API-coated granules. Alternatively, the dried granules may be pressed into a tablet. See, J. K. Lalla & Shruti U. Bhat, Controlled-Release Isosorbide Dinitrate Pellets. Part I: Design and Evaluation of Controlled-Release Capsule Dosage Form, J. Pharm. Sci., 82(12):1288-1291 (1993); J. K. Lalla & Shruti U. Bhat, Controlled-Release Isosorbide Dinitrate Pellets. Part II: In Vivo Studies, J. Pharm. Sci., 82(12): 1292-1295 (1993), both of which are hereby incorporated by reference.

U.S. Pat. No. 5,968,554 to Beiman, et al. teaches a multi-layered controlled release dosage capable of delivering a pharmaceutical to both the stomach and the duodenum. Similarly, U.S. Pat. No. 6,312,728, also to Beiman, et al., teaches a multi-layered controlled release dosage capable of delivering a pharmaceutical to both the duodenum and large intestine or colon or to the stomach, duodenum, and large intestine or colon. Both references are incorporated herein by reference.

A number of related controlled-release dosages and methods have been described by Percel et al. For example, U.S. Pat. No. 6,627,223 describes a pharmaceutical dosage comprised of timed, sustained-release (TSR) beads having at least two coated membrane barriers, the composition and thickness of the barriers determining the lag time and duration of drug release. In one embodiment, a first membrane barrier is an enteric polymer and a second membrane is a mixture of a water-insoluble polymer and an enteric polymer. Such a configuration permits one or more pulses of a therapeutic agent in a plasma concentration-time profile.

U.S. Pat. No. 6,500,454, also to Percel et al., describes a dosage unit for providing a circadian-like release of propranolol to mimic the time-dependent physiological need for the drug. U.S. Pat. No. 6,663,888, also to Percel et al., describes a similar dosage for the circadian-like release of a histamine H2 antagonist. Each of the Percel et al. references above is incorporated herein by reference.

Other controlled-release methods known in the art are within the scope of the present invention, including, for example, conventional pan coating, perforated pan coating, fluidized-bed coating, top-spray coating, bottom-spray coating, and tangential-spray coating. See, e.g., Atul M. Mehta & David M. Jones, Coated Pellets Under the Microscope, Pharm. Tech., June 1985, which is also hereby incorporated by reference. Various excipients may be incorporated into the controlled-release dosage form of the invention. Such excipients include, for example, Eudragit® polymers (Rohm & Haas), ethylcellulose, Ethocel® polymers (Dow Chemical Company), triethyl citrate, hydroxypropyl methylcellulose (HPMC), polyvinylpyrrolidone (PVP), sugars, and acidic buffering agents. Generally, such excipients would comprise the bulk of a controlled-release dosage.

In an alternative illustrative embodiment, a controlled release dosage form of the invention is designed to provide intermittent, or pulsatile, release of drug. In such embodiment, the dosage form may release 2, 3, 4, 5, or even 6 aliquots of drug over a period of several hours, e.g., 2-24 hours, 8-24 hours, or 16-24 hours. An illustrative pulsatile delivery dosage form of the invention releases drug in 3 aliquots, each in a separate "compartment," one that releases drug primarily in the duodenum, a second that releases drug primarily in the jejunum, and a third that releases drug primarily in the ileum. The amount of drug released in each aliquot can be an equal fraction of the total amount or the amounts can be different. In pulsatile release embodiments of this invention, the choice of buffering agent and counterion can differ for the different aliquots, depending, for example, on where in the GI tract a particular aliquot is expected to be released.

Various formulations and methods of administering iloperidone have been described. For example, PCT Application Publication No. WO2004/006886A2 describes an injectable depot formulation comprising iloperidone crystals; microencapsulated depot formulations of iloperidone and a polyglycolide polylactide glucose star polymer are described in U.S. Patent Application Publication No. 20030091645; and methods for the administration of iloperidone directed toward, inter alia, eliminating or minimizing the prolongation of a corrected electrocardiographic QT (QTc) interval associated with increased concentrations of iloperidone or iloperidone derivatives are described in U.S. Provisional Patent Application No. 60/614,798, filed 30 Sep. 2004, all of which are incorporated herein by reference.

In another illustrative embodiment, the invention comprises a kit further comprising one or more pharmaceutical dosage units of 4-[3-[4-(6-fluoro-1,2,-benzisoxazol-3-yl)-1-piperidinyl]propoxyl]-3-methoxy-benzoic acid and, optionally, one or more pharmaceutical dosage units of an antithrombic agent. In another embodiment, the invention comprises administering 4-[3-[4-(6-fluoro-1,2,-benzisoxazol-3-yl)-1-piperidinyl]propoxy]-3-methoxy-benzoic acid dosage units and the antithrombic agent dosage units at different time periods, such that an effective amount of each is maintained in the patient's bloodstream in the appropriate amounts at the appropriate times.

In a related embodiment, a kit comprises pharmaceutical dosage units of one agent alone and other pharmaceutical dosage units comprising both agents. Such a kit could facilitate the administration of 4-[3-[4-(6-fluoro-1,2,-benzisoxazol-3-yl)-1-piperidinyl]propoxyl]-3-methoxy-benzoic acid at different time intervals than the antithrobmic agent(s).

When used in such combinations, the dose of each agent is expected to be approximately the same as, or less than, an effective amount of either alone. For example, each pharmaceutically active ingredient can be administered in doses that are about 20% to about 80% of the dose in which each ingredient would be administered alone.

The two (or more) agents can be administered more or less simultaneously, i.e., concomitantly (e.g., within about 0 to about 5 minutes of each other, preferably within about a minute apart), or they can be administered at different times. For example, the compositions can be formulated in a unit dosage form, each dosage containing both active ingredients. The term "unit dosage form" refers to physically discrete units suitable as unitary dosages for human subjects and other animals, each unit containing a predetermined quantity of active material calculated to produce the desired prophylactic or therapeutic effect over the course of a treatment period, in association with the required pharmaceutical carrier.

Unit dosage forms of the invention, whether they comprise 4-[3-[4-(6-fluoro-1,2,-benzisoxazol-3-yl)-1-piperidinyl]propoxyl]-3-methoxy-benzoic acid as the sole active pharmaceutical ingredient or in combination with another agent, can also be formulated in a controlled release form, e.g., delayed, sustained, or pulsatile release. With such form, in the case of combinations, 4-[3-[4-(6-fluoro-1,2,-benzisoxazol-3-yl)-1-piperidinyl]propoxyl]-3-methoxy-benzoic acid can be released at the same or different rates and times as the other agent or agents.

In other embodiments, the invention comprises a medicated device, e.g., an implantable medical device, comprising 4-[3-[4-(6-fluoro-1,2,-benzisoxazol-3-yl)-1-piperidinyl]propoxy]-3-methoxy-benzoic acid or a pharmaceutically-acceptable salt thereof. Such medicated device can be any medical device that is placed within a subject such as by implantation or insertion. The device may be inside the subject for any length of time, depending, e.g., on the particular device that is being utilized and the condition that is being treated. In specific illustrative embodiments, the device is a catheter, stent, guidewire, sensor, ventricular assist device, graft, valve such as an aortic valve, pacemaker, artificial joint, or infusion system/pump. Such devices having an API that releases from the device are commonly referred to a drug-eluting devices. Various methodologies are available for fabricating a drug-eluting medical device, including coating the API on a surface of the device, formulating the API in a polymer matrix and holding the matrix in a receptacle in the device, impregnating a porous medical device with a formulation comprising the API, etc.

In a particular illustrative embodiment, the invention comprises a drug eluting stent that is coated on the inside or outside surfaces, or both, with a polymeric matrix comprising 4-[3-[4-(6-fluoro-1,2,-benzisoxazo1-3-yl)-1-piperidinyl]propoxyl]-3-methoxy-benzoic acid or a pharmaceutically-acceptable salt thereof. Such device is useful for opening "clogged" blood vessels and preventing or delaying, or reducing the risk of, restenosis.In a related aspect, this invention comprises a method of promoting, marketing, or selling a pharmaceutical composition comprising 4-[3-[4-(6-fluoro-1,2,-benzisoxazol-3-yl)-1-piperidinyl]propoxy]-3-methoxy-benzoic acid or a pharmaceutically-acceptable salt thereof that comprises disseminating information to prospective patients, formulary managers, or physicians or other prescribers about the compound, such information including that 4-[3-[4-(6-fluoro-1,2,-benzisoxazol-3-yl)-1-piperidinyl]]propoxy]-3-methoxy-benzoic acid or a pharmaceutically-acceptable salt thereof has a receptor antagonist profile as described above and, specifically, is a potent antagonist of the 5HT$_{2A}$ receptor. In a related aspect, the invention comprises a system for disseminating such information, such system comprising, for example, a data storage medium wherein such information is stored, a means for retrieving such information from the data storage medium, such as a computer, and a means for disseminating the retrieved information to relevant persons, such as by sending the information electronically or by printing and physically distributing copies of the printed information.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of antagonizing a 5-HT$_{2A}$ receptor in an animal, the method comprising:
    internally administering to the animal an effective amount of 4-[3-[4-(6-fluoro-1,2,-benzisoxazol-3-yl)-1-piperidinyl]propoxy]-3-methoxy-benzoic acid or pharmaceutically-acceptable salt thereof.

2. The method of claim 1, wherein the 5-HT$_{2A}$ receptor is not located in the brain.

3. The method of claim 1, wherein the 4-[3-[4-(6-fluoro-1,2,-benzisoxazol-3-yl)-1-piperidinyl]propoxy]-3-methoxy-benzoic acid or pharmaceutically-acceptable salt thereof administered to the animal is between about 1 mg/day and about 500 mg/day.

4. The method of claim 3, wherein the effective amount is between about 5 mg/day and about 100 mg/day.

5. The method of claim 1, wherein the effective amount of 4-[3-[4-(6-fluoro-1,2,-benzisoxazol-3-yl)-1-piperidinyl] propoxy]-3-methoxy-benzoic acid or pharmaceutically-acceptable salt thereof administered to the animal is between about 0.01 mg/kg/day and about 10 mg/kg/day.

6. The method of claim 5, wherein the effective amount is between about 0.5 mg/kg/day and about 1.5 mg/kg/day.

7. The method of claim 1, wherein the animal is a human.

8. A method of antagonizing a 5-HT$_{2A}$ receptor in an animal, the method comprising:
    internally administering to the animal an effective amount of 4-[3-[4-(6-fluoro-1,2,-benzisoxazol-3-yl)-1-piperidinyl]propoxy]-3-methoxy-benzoic acid or pharmaceutically-acceptable salt thereof,
    wherein the animal is suffering from a condition selected from the group consisting of: platelet aggregation, coronary artery disease, myocardial infarction, transient ischemic attacks, stable angina, unstable angina, thrombotic stroke, a secondary ischemic event, atrial fibrillation, thrombosis, restenosis, asthma, diabetic nephropathy, and diabetic retinopathy.

9. The method of claim 8, wherein the secondary ischemic event is selected from the group consisting of: reversible ischemic neurological deficit and intermittent claudication.

10. The method of claim 8, wherein thrombosis is clot formation associated with at least one of the following: angioplasty, cardiac surgery, or atrial fibrillation.

11. The method of claim 8, wherein the condition is restenosis as a result of treatment with a medicated device.

12. The method of claim 11, wherein the medicated device is a medicated stent.

13. A method of antagonizing a 5-HT$_{2A}$ receptor in an animal, the method comprising:
    internally administering to the animal an effective amount of 4-[3-[4-(6-fluoro-1,2,-benzisoxazol-3-yl)-1-piperidinyl]propoxy]-3-methoxy-benzoic acid or pharmaceutically-acceptable salt thereof; and
    administering to the animal at least one antithrombotic agent.

14. The method of claim 13, wherein the antithrombotic agent is selected from the group consisting of: clopidogrel bisulfate, streptokinase, alteplase, aprotinin, aspirin, and warfarin.

* * * * *